United States Patent [19]
Nagai et al.

[11] Patent Number: 5,464,816
[45] Date of Patent: Nov. 7, 1995

[54] METHOD AND PHARMACEUTICAL COMPOSITIONS FOR TREATING IMMUNODEFICIENCIES

[75] Inventors: Yoshitaka Nagai, Tokyo; Hayao Abe, Chiba; Masanobu Arita, Kanagawa, all of Japan

[73] Assignee: Mitsui Pharmaceuticals Inc., Tokyo, Japan

[21] Appl. No.: 498,637

[22] Filed: Mar. 26, 1990

Related U.S. Application Data

[63] Continuation of Ser. No. 734,259, May 15, 1985, Pat. No. 5,112,810.
[51] Int. Cl.⁶ .......................... A61K 38/04; A61K 38/08
[52] U.S. Cl. ................................ 514/2; 514/15; 514/885; 514/903; 424/531; 424/580
[58] Field of Search ............................. 514/15, 885, 903; 424/531, 580

[56] References Cited

U.S. PATENT DOCUMENTS

| | | | |
|---|---|---|---|
| 4,133,804 | 1/1979 | Bach et al. | 424/531 |
| 4,229,438 | 10/1980 | Fujino et al. | 424/177 |

FOREIGN PATENT DOCUMENTS

| | | |
|---|---|---|
| 2512975 | 10/1975 | Germany . |
| 2732587 | 3/1978 | Germany . |
| 2822951 | 12/1978 | Germany . |
| 2919218 | 11/1979 | Germany . |
| 54148725 | 9/1981 | Japan . |
| 56-148725 | 9/1981 | Japan . |

OTHER PUBLICATIONS c.f. G. Kuroiwa, "Intractable Diseases—Study & Prospect", S. Okinada, Ed., Tokyo Univ. Press, 1979, pp. 7–27, 1979.
Freund et al. (J. Freund et al., J. Immunol., 57, 179, 1947).
Kabat et al., E. A. Kabat et al., J. Exp. Med., 85, 117, 1947.
Morgan et al., J. Exp. Med., 85, 131, 1947.
c.f. A. N. Davison and M. L. Cuzner, Ed., "The Suppression of Experimental Allergic Encephalomyelitis and Multiple Sclerosis", Academic Press, 1980.
S. Levine and R. Sowinshi, J. Immunol., 120, 602, 1978.
P. Y. Paterson and D. Drobish, Science, 165, 191, 1969.
P. Y. Paterson et al., J. Immunol., 118, p. 2151, 1977.
C. A. Bernard et al., Int. Arch. Allegy Appl. Immunol., 53, p. 555, 1977.
R. Arnon & D. Teitelbaum, "The Suppression of Experimental Allergic Encephalomyelitis and Multiple Sclerosis", Academic Press, p. 105, 1980.
M. A. Bach, Lancet, Dec., p. 1221, 1980.
Reinherz et al., New Engl. J. Med., 303, p. 125, 1980.
J. F. Bach et al., Nature, 266, p. 55, 1977.
Jean–Marie Pleau et al., J. Boil. Chem., 252, p. 8045, 1977.
Nagai et al., Adv. in Neurol. Sci. (Japan), 23, p. 1001, 1979.
V. A. Coates et al., Cell, Immunol. 12, p. 370, 1974.
L. A. Autilio et al., J. Neurochemistry, 11, 17, 1964.
T. Iwata et al., Am. J. of Medicine, 71, pp. 385–394.
W. Cendrowski, Archives Suisses de Neurologie, Neurochirugie et de Psychiatrie 127, pp. 199–203, 1980.
Bordigoni et al., The Lancet, Aug. 7, 1982, pp. 293–297.
Bach et al., in Immunoregulation and Autoimmunity, ©1980 Elsevier Press, pp. 221–230.

*Primary Examiner*—Suzanne E. Ziska
*Attorney, Agent, or Firm*—Birch, Stewart, Kolasch & Birch

[57] ABSTRACT

A pharmaceutical composition containing serum thymic factor (FTS) and a method for using FTS containing compositions for treating a variety of immunodeficiencies and autoimmune diseases including multiple sclerosis, Guillain-Barré syndrome, inflammatory neuropathy, polyneuritis and other immunodemyelinating diseases.

2 Claims, No Drawings

METHOD AND PHARMACEUTICAL COMPOSITIONS FOR TREATING IMMUNODEFICIENCIES

This application is a continuation, of application Ser. No. 06/734,299 filed on May 15, 1985, U.S. Pat. No. 5,112,840.

BACKGROUND AND FIELD OF THE INVENTION

The present invention relates to a method and composition for treating multiple sclerosis, demyelinating diseases and other diseases belonging to the general category of immunodeficiency diseases.

Multiple sclerosis, one of the demyelinating diseases of unknown etiology, has been known as one of the most intractable diseases known in the world with no effective therapy having yet been developed for it (c.f.G. Kuroiwa, "Intractable Diseases-Study and Prospect", S. Okinaka, Ed., Tokyo Univ. Press, 1979, pp. 7–27, 1979).

For allergic demyelinating diseases in humans, however, a useful experimental model was developed in 1947 by three research groups independently but having recourse to the same technique. Freund et al. (J. Freund et al., J. Immunol. 57, 179, 1947), Kabat et al. (E. A. Kabat et al., J. Exp. Med., 85, 117, 1947) and Morgan et al. (I. M. Morgan et al., J. Exp. Med., 85, 131, 1947) disclosed the successful development of experimental allergic encephalomyelitis (EAE) in animals by injecting a homogenized emulsion of the animal brain employing Freund's complete adjuvant technique, and the death of the animals within two or three weeks of the treatment. Since then, EAE has been utilized as an experimental model in studies of multiple sclerosis and other diseases influenced by cellular immunodeficiency. Indeed, it has served as a rare and useful system for in vivo-screening of curatives and treatments for demyelinating diseases and other immunodeficiency and autoimmune diseases.

Drugs for which EAE has been employed as a screening system include steroid anti-inflammatory agents, nonsteroid anti-inflammatory agents such as Flubiprofen, Cyclosporin A (cf. A. N. Davison and M. L. Cuzner, Ed. "The Suppression of Experimental Allergic Encephalomyelitis and Multiple Sclerosis" Academic Press, 1980), and E. N. 3638 (S. Levine and R. Sowinshi, J. Immunol. 120, 602, 1978; P. Y. Paterson and D. Drobish, Science, 165, 191, 1969), Cyclophosphamide (S. Levine and R. Sowinshi, J Immunol 120, 602 1978), Nitridazole (P. Y. Paterson et al., J. Immunol., 118. p. 2151, 1977 and C. A. Bernard et al., Int. Arch. Allergy Appl. Immunol., 53, p. 555, 1977) and amino acid copolymer (R Arnon and D. Teitelbaum, "The Suppression of Experimental Allergic Encephalomyelitis and Multiple Sclerosis", Academic Press, p. 105, 1980). The responses of EAE against these drugs in screening processes have probably been due to the immunosuppressive effects of the drugs. Of these drugs, however, those which presented any positive effects were of the steroid family.

In inflammatory or rheumatic diseases, some steroids also work remarkably well. However, undesirable secondary effects are almost always involved in their clinical application so that the drugs of this family are gradually being replaced by newly developed non-steroidal ones. For multiple sclerosis and other autoimmune diseases, the development of non-steroidal drugs that would act efficaciously but not be accompanied by adverse side effects in therapy is likewise desired.

As a result of recent researches, multiple sclerosis has come to be recognized as a disease caused by viral infection and/or the malfunction of thymus dependent lymphocytes (T-cell) in which the problem resides in a reduction in the number of "suppressor T-cells" (M. A. Bach, Lancet, December, p. 1221, 1980 and Reinherz et al., New Engl. J. Med., 303, p. 125, 1980). As for biosubstances involved in the control, differentiation and function of T-cells, some high molecular weight proteins such as thymosin have become known in recent studies.

In 1976, a nonapeptide having an amino acid sequence: p-Glu-Ala-Lys-Ser-Gln-Gly-Gly-Ser-Asn-OH (p-Glu representing pyroglutamic acid) was isolated from a volume of pig serum by J. F. Bach et al., and was named Facteur Thymique Serique (FTS) or Serum Thymic Factor (J. F. Bach et al., Nature, 266, p. 55, 1977 and Jean-Marie Pleau et al., J. Biol. Chem. 252, p. 8045, 1977). The present invention then is directed to new uses and pharmaceutical compositions containing FTS. FTS has been thought to have the ability to efficiently induce T-cell differentiation and some researchers seem to think that there may be low molecular weight peptides in mice, humans and other animals which might have actions similar to FTS. The present inventors have for some years been conducting research relative to the low molecular peptide: FTS for applications to the therapy of multiple sclerosis and other immunodeficiencies. The discovery of the in vivo effects of FTS in delaying the onset of neurological and clinical signs in EAE guinea pigs and monkeys, in alleviating the symptoms and greatly increasing survival time and in the cure-rate of treated animals led them to work out the present invention.

An EAE system utilizable in laboratory study can be obtained in almost any species of animals when they are immunized with an extract of the animal brain such as the myelin basic protein emulsified in the Freund's complete adjuvant formulation. The most frequently employed systems are those in guinea pigs, mice and monkeys In guinea pigs that are immunized in this way the clinical symptoms of EAE generally develop rather acutely. The animals cease to show notable body weight gain and, at about the tenth day after immunization, the animals begin to lose weight. At about the twelfth day, ataxia and paralysis develop in the hind part of the bodies and death comes to each one thereafter. The observed symptoms are similar in mice although death does not necessarily follow and many have a chance to recover when diet and other conditions are improved.

In guinea pigs, recent progress in research has made it possible to develop, besides the rather acute type of EAE which causes the animals to die within ten to sixteen days after immunization, a more chronic type of EAE which manifests a retarded onset of the symptoms and the occurrence of death. This chronic type of EAE was developed by modifying the immunization technique and adjusting animal conditions including the selection of their age. A guinea pig in which such a rather chronic type of EAE is induced shows symptoms which more closely resembled multiple sclerosis of humans.

At this time, however, only the conventional, rather acute type of EAE animal system is generally employed by medical and pharmaceutical specialists for screening new drugs to be employed in the treatment of EAE. Even new curatives for treating EAE, including steroids, which have been developed under such circumstances continue to give only a limited contribution to the prolongation of the lives of animals suffering from demyelinating diseases or other diseases of this category.

OBJECTS AND SUMMARY OF THE INVENTION

It is therefore one object of the present invention to provide a pharmaceutical composition containing serum thymic factor (FTS).

It is another object of the present invention to provide a method and pharmaceutical composition containing FTS for the treatment of multiple sclerosis, Guillain-Barré syndrome, inflammatory neuropathy, polyneuritis, and other immunodemyelinating diseases and other diseases involving immunodeficiencies.

These and other objects of the present invention are accomplished by a pharmaceutical composition containing serum thymic factor (FTS) which can be utilized in treating various demyelinating diseases and other immunodeficiencies and autoimmune diseases.

DETAILED DESCRIPTION OF THE INVENTION

The present invention specifically relates to the development of an excellent pharmaceutical composition for treating multiple sclerosis containing FTS as the active ingredient. This composition has the ability to cause EAE guinea pigs to survive up to thirty or even thirty-five days after immunization which is longer than results previously reported for other treatments. The curative effect actually displayed in prolonging the survival of EAE guinea pigs is summarized as follows.

Of ten guinea pigs pretreated subcutaneously with FTS at a dose as low as 10 μg on a day before immunization (Day −1) and further treated with 10 μg FTS on Days 4, 10 and 17, six were still alive on Day 30 (Group II, Table 1). In another group of ten animals, FTS was administered in a dose of 10 μg on every fourth day beginning from Day 9 after immunization, and two out of the ten animals were still alive on Day 30 (Group III, Table 1). The results of these experiments show that the effect of FTS was higher when the treatment was commenced earlier, that is prior to immunization. But even if the treatment was commenced just before the onset of the disease symptoms, the curative effect of administering FTS was sufficient to maintain some of the animals alive on Day 30.

In another experiment treating EAE guinea pigs, divided into groups of five animals each, FTS was administered consecutively in a daily dose of 50 μg, commencing the treatment on Days −2, 0 and 6, and ending in each case on Day 14. The efficacy of the FTS treatment was displayed in that two or three animals from each treatment group were still alive on Day 35 of the experiment (Groups IV, V & VI, Table 4).

Whereas incontinence or diarrhea was observed in EAE guinea pigs receiving no curative treatment and the animals died after developing a critical symptom (Group I, Tables 1 and 4), only a minor pathological picture was presented by the FTS-treated animals. Even if an FTS-treated animal presented a relatively grave pathology similar to that shown in the untreated animals, the sound life prolonging effect and body weight gain were still clearly observed.

As described above, FTS acted to inhibit the onset of the EAE symptoms in guinea pigs and to produce a remarkable effect in alleviating the EAE symptoms. The significant effect of FTS treatment in considerably extending the interval between the first appearance of EAE symptoms and death was also manifest in monkeys.

The conspicuous activity of FTS in inducing T-cell differentiation has heretofore only been displayed in the experimental system of the mouse. Accordingly, the fact that its remarkable effects on EAE therapy and survival of animals were first ascertained in experimental guinea pig and monkey systems is important since EAE in guinea pigs and monkeys is considered to more closely resemble allergic encephalomyelitis of humans. It is also important that there has been no drug except for the drug of the present invention and those of the steroid group that have manifested any notable efficacy in the EAE screening system.

Since EAE is considered, by some specialists, partially to be a T-cell mediated autoimmune disease, the positive responses of EAE animals against FTS is considered also as a proof of the restoration of the balance of the immune system in the animals. FTS, being a natural biosubstance, has no adverse effects so that it is considered to be useful for the clinical treatment of multiple sclerosis, Guillain-Barre syndrome, inflammatory neuropathy, polyneuritis, and other immunodemyelinating diseases and other diseases involving immunodeficiencies.

Diseases to which the application of FTS are envisioned include systemic lupus erythematodes, Di George's syndrome, chronic dermato/muco candiadis, progressive nervous degeneration, skin and eyeball telangiectasia, ataxia-telangiectasis, thrombopenia, eczema, Wiskoff-Aldrich syndrome frequently involving infections, some immunodeficiency involving thymoma and cancer.

Various analogues of FTS are possible by replacing a part of its amino acid sequence with other amino acids. These analogues are looked upon with great expectations since some of them may prove similarly useful or even more efficacious in therapy. Some humoral components other than FTS including thymosin $\alpha_1$, thymosin fraction 5 and various so-called thymic hormones are also looked upon with the idea that they will have some therapeutical effects on multiple sclerosis and other immunodeficiencies. Of these, some of the thymic hormones were reported in literature in relation to some studies in Di George's syndrome treatment but all the other substances have not yet been subjected to intensive therapy studies in any country. Since these compounds are generally polymers of a higher molecular weight compared to FTS, the problem of antigenicity may occur, and in cases where they are of non-human origin, they may give rise to allergic or anaphylactic developments.

FTS can be isolated from a large quantity of serum but is also available by ordinary chemical synthesis involving solid or liquid phase reactions. It can also be prepared by a genetic-engineering process and/or a cell-fusion process.

FTS can be administered to patients as is or in the form of any pharmaceutically acceptable salt and by a parenteral route. It can be injected intravenously, intramuscularly or subcutaneously, or be employed in the form of a suppository. In an intravenous or intramuscular injection, a daily dose in the range of 0.1– 100 μg/kg is sufficient although it depends on the condition of the patient and the duration of the treatment with the drug. It can be administered singly or in a formulation with agents which act as immunopotentiators.

The pharmaceutical composition of the invention will now be more fully described with reference to examples embodying the invention but which are intended to be illustrative only, and the invention is not limited thereto.

Example 1. FTS injection in vial 5 mg of sterilized FTS•$CH_3COOH$-$2H_2O$ (Peptide Institute, Inc.) is filled in a vial and lyophilized.

Example 2. FTS injection in ampoule 20 mg FTS·CH$_3$COOH·$_2$H$_2$O is dissolved in physiological saline solution and sterilized with a filter and filled in an ampoule.

The following is a description of tests, and the results therefrom, which were performed to test the usefulness of FTS in the treatment of immunodemyelinating diseases and other diseases involving immunodeficiencies.

Experiment 1 Effect of 10 μg FTS Administered to EAE Guinea Pigs

(i) EAE induction (Nagai's method)

In accordance with the method described by Nagai et al. (Adv. in Neurol. Sci. (Japan) 23, p. 1001, 1979), each animal was inoculated in the foot pads with an emulsion prepared from 30 μg myelin basic protein (MBP) from the bovine brain mixed with the Freund's complete adjuvant containing 100 μg killed mycobacterium tuberculosis AOYAMA B.

The day of the MDP inoculation was taken as the start of the experiment or Day 0.

(ii) Guinea pigs

Male Hartley guinea pigs, 5 weeks of age, weighing 260–340 g were employed. They were divided into three groups of ten animals with one group serving as control.

(iii) FTS administration

FTS, dissolved in a phosphate buffered physiological saline solution (PBS) at the concentration of 20 μg in 1 ml and stored at −20° C., was thawed and immediately injected into the animals of two treatment groups. Each of the animals received a single daily dose of 0.5 ml (10 μg) s.c. on the back.

(iv) Assessment

1. Body weights

Body weights of the control and treatment animals were inspected daily and compared. Progress of individual body weight was registered in tables, expressed in percentage of the Day 0 body weight.

2. Clinical symptoms of animals:

The animals were observed daily. Clinical signs were graded numerically by Coates' method (V. A. Coates et al., Cell. Immunol. 12, p. 370, 1974) according to the degree of severity of the clinical signs developed in the animals as described below. Clinical signs were also noted for animals receiving no FTS treatment (control group animals).

| Disease Severity Scoring of Clinical Signs | |
|---|---|
| Score | Sign |
| blank | no clinical disease |
| 1 | a reduced motility accompanying a body weight loss |
| 2 | hind limb weakness |
| 3 | hind limb paralysis |
| 4 (or D) | death |
| Δ | incontinence and diarrhea involved with the score 2 or 3 |

3. Histopathological signs of EAE

Histopathological inspection of the brain and spinal chord was conducted in 10 % formalin-fixed specimens obtained from the FTS-treated as well as non-treated control guinea pigs with results graded as follows (results are reported in Table 6).

| Histopathological Scoring | |
|---|---|
| Score | |
| 0 (or blank) | no lymphocyte accumulation observed in vascular wall |
| + | occasional perivascular lymphocyte accumulation |
| ++ | frequent lymphocyte infiltration in most perivascular regions |
| +++ | severe perivascularlymphocyte infiltration around almost every vessel |

The results of Experiment 1 are reported in Tables 1, 2, 3 and 6.

Experiment 2 Effect of 50 μg FTS Administered to EAE Guinea Pigs

Experiment 2 was conducted in the same manner as in Experiment 1 except that the amount of FTS dissolved in 1 ml PBS was 100 μg so that the dosage administered to the treatment animals was 50 μg. The results are presented in Tables 4, 5 and 6.

Experiment 3 Toxicity

Toxicity was studied by treating a male Hartley guinea pig with FTS at a dose of 100 mg/kg and observing the animal for one-week. This animal was still alive at the end of one-week observation period.

TABLE 1

Effects of FTS on EAE Guinea Pigs
(10 μg/day, animal)

| Group | Dose μg/day, animal | No. of animals | Average day for the first sign of EAE after immunization | Days after immunization when death occurred in an animal | Mortality and survival. No. of animals 30 days after immunization | | |
|---|---|---|---|---|---|---|---|
| | | | | | dead | survived | (Surv. %) |
| I | 0 | 9 | 11.7 | 10, 12, 13, 13, 13, 13, 14, 14, 16 | 9/9 | 0/9 | (0) |
| II | 10 | 10 | 16.7 | 14, 16, 17, 18, >30, >30, >30, >30, >30, >30 | 4/10 | 6/10 | (60) |
| III | 10 | 10 | 12.9 | 11, 13, 13, 13, 16, 16, 18, 21, >30, >30 | 8/10 | 2/10 | (20) |

FTS injection: Group I: none
Group II: at Days −1, 4, 10, 17.
Group III: at Days 9, 12, 15, 18, 21, 24.
Experiment ended on Day 30.

TABLE 2

Body Weight Gain in EAE Guinea Pigs of Group I with No FTS Treatment

Group I — Body weight: (g); Rate of gain: (%); Clinical findings: blank ... no anomaly; 1, 2, 3 or Δ ... as stated in "Experiment 1"; D: death.

| Days after immunization | 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| Guinea pig (g) No. 1 | 319 | 315 | 325 | 322 | 328 | 340 | 340 | 346 | 348 | 357 | 358 | 352 | 345 | 340 | 341 | 310 | 270 |
| (%) | 100 | 99 | 102 | 101 | 103 | 107 | 107 | 109 | 109 | 112 | 112 | 110 | 108 | 107 | 107 | 97 | 85 |
| Clinical findings | | | | | | | | | | | | | | | | 2 | 2D Δ |
| Guinea pig (g) No. 2 | 314 | 304 | 310 | 312 | 320 | 322 | 328 | 337 | 342 | 335 | 324 | 290 | 260 | | | | |
| (%) | 100 | 97 | 99 | 99 | 102 | 103 | 105 | 107 | 109 | 107 | 103 | 92 | 83 | | | | |
| Clinical findings | | | | | | | | | | 1 | 1 | 1 | 3D | | | | |
| Guinea pig (g) No. 3 | 282 | 260 | 275 | 270 | 285 | 295 | 300 | 298 | 305 | 305 | 305 | 305 | 285 | 255 | | | |
| (%) | 100 | 92 | 98 | 96 | 101 | 105 | 106 | 106 | 108 | 108 | 108 | 108 | 101 | 90 | | | |
| Clinical findings | | | | | | | | | | 1 | 1 | 1 | 2 Δ | 3D Δ | | | |
| Guinea pig (g) No. 4 | 310 | 295 | 300 | 305 | 315 | 320 | 330 | 330 | 315 | 325 | 325 | 335 | 334 | 290 | | | |
| (%) | 100 | 95 | 97 | 98 | 102 | 103 | 107 | 107 | 102 | 105 | 105 | 108 | 108 | 94 | | | |
| Clinical findings | | | | | | | | | | | | | 1 | 3D Δ | | | |

TABLE 3

Body Weight Gain in EAE Guinea Pigs of Group II Treated with FTS
(10 μg/day, animal)

Group II — Body weight: (g); Rate of gain: (%); Clinical findings: blank ... no anomaly; 1, 2, 3 or Δ ... as stated in "Experiment 1"

| Days after immunization | −1↑ | 0 | 1 | 4↑ | 5 | 8 | 10↑ | 13 | 14 | 15 | 17↑ | 19 | 21 | 22 | 23 | 24 | 25 | 29 | 30 |
|---|---|---|---|---|---|---|---|---|---|---|---|---|---|---|---|---|---|---|---|
| Guinea Pig (g) No. 1 | 330 | 337 | 325 | 365 | 380 | 410 | 430 | 404 | 407 | 430 | 420 | 425 | 350 | 319 | — | 300 | 305 | — | 352 |
| (%) | | 100 | 96 | 108 | 113 | 122 | 128 | 120 | 121 | 128 | 125 | 126 | 104 | 95 | — | 89 | 91 | — | 105 |
| Clinical findings | | | | | | | | | | | 1 | | 1 | | | | | | |
| Guinea Pig (g) No. 2 | 300 | 306 | 290 | 332 | 330 | 368 | 368 | 315 | 307 | 290 | 200 | 242 | 284 | 278 | — | 260 | 270 | — | 300 |
| (%) | | 100 | 95 | 109 | 108 | 120 | 120 | 103 | 100 | 95 | 65 | 79 | 93 | 91 | — | 85 | 88 | — | 98 |
| Clinical findings | | | | | | | | | | 3 | Δ | | | | | | | | |
| Guinea Pig (g) No. 3 | 274 | 293 | 280 | 316 | 325 | 330 | 349 | 365 | 372 | 376 | 360 | 275 | 307 | 340 | — | 340 | 345 | — | 378 |
| (%) | | 100 | 96 | 108 | 111 | 113 | 119 | 125 | 127 | 128 | 123 | 94 | 105 | 116 | — | 116 | 118 | — | 129 |

TABLE 3-continued

Body Weight Gain in EAE Guinea Pigs of Group II Treated with FTS
(10 μg/day, animal)

Group II
Days after immunization

Body weight: (g)
Rate of gain: (%)
Clinical findings: blank . . . no anomaly; 1, 2, 3 or Δ . . . as stated in "Experiment 1"

| Days after immunization | −1↑ | 0 | 1 | 4↑ | 5 | 8 | 10↑ | 13 | 14 | 15 | 17↑ | 19 | 21 | 22 | 23 | 24 | 25 | 29 | 30 |
|---|---|---|---|---|---|---|---|---|---|---|---|---|---|---|---|---|---|---|---|
| Clinical findings | | | | | | | | | | | 1 Δ | 2 Δ | 1 | | | | | | |

Data for Days 2, 3, 6, 11, 27 and 28 omitted.
↑: FTS injection
—: No observation performed.

TABLE 4

Effects of FTS on EAE Guinea Pigs
(50 μg/day, animal)

| Group | Dose μg/day, animal | No. of animals | Average day for the first sign of EAE after immunization | Days after immunization when death occurred in an animal | Mortality and survival. No. of animals 30 days after immunization | | |
|---|---|---|---|---|---|---|---|
| | | | | | dead | survived | (Surv. %) |
| I | 0 | 9 | 11.7 | 10, 12, 13, 13, 13, 13, 14, 14, 16 | 9/9 | 0/9 | (0) |
| IV | 50 | 5 | 15.7 | 17, 18, 23, >35, >35 | 3/5 | 2/5 | (40) |
| V | 50 | 5 | 18.0 | 20, 22, >35, >35, >35, | 2/5 | 3/5 | (60) |
| VI | 50 | 5 | 19.0 | 23, 30, >35, >35, >35 | 2/5 | 3/5 | (60) |

FTS injection:
Group I; None.
Group IV; Daily from the Day −2 to 14.
Group V; Daily from the Day 0 to 14.
Group VI; Daily from the Day 6 to 14.
Experiment ended on Day 35.

TABLE 5

Body Weight Gain in EAE Guinea Pigs of Group V Treated with FTS
(50 μg/day, animal)

Group V

Body weight: (g)
Rate of gain: (%)
Clinical findings: blank . . . no anomaly; 1, 2, 3 or Δ . . . as stated in "Experiment 1" D:death.

| Days after immunization | 0↑ | 1↑ | 4↑ | 5↑ | 7↑ | 8↑ | 9↑ | 10↑ | 11↑ | 12↑ | 13↑ | 14↑ |
|---|---|---|---|---|---|---|---|---|---|---|---|---|
| Guinea Pig (g) No. 1 (%) Clinical findings | 310 100 | 310 100 | 325 105 | 345 111 | 355 115 | 370 119 | 380 123 | 385 124 | 385 124 | 395 127 | 405 131 | 405 131 |
| Guinea Pig (g) No. 2 (%) Clinical findings | 312 100 | 310 99 | 345 111 | 355 114 | 370 119 | 380 122 | 390 125 | 405 130 | 415 133 | 415 133 | 420 135 | 425 136 |
| Guinea Pig (g) No. 3 (%) Clinical findings | 305 100 | 315 108 | 355 116 | 360 118 | 375 123 | 400 131 | 405 133 | 410 134 | 425 139 | 430 141 | 435 143 | 445 146 |
| Guinea Pig (g) No. 4 (%) Clinical findings | 305 100 | 333 109 | 365 120 | 370 121 | 390 128 | 410 134 | 410 134 | 425 139 | 425 139 | 430 141 | 440 144 | 455 149 |

Group V

Body weight: (g)
Rate of gain: (%)
Clinical findings: blank . . . no anomaly; 1, 2, 3 or Δ . . . as stated in "Experiment 1" D:death.

| Days after immunization | 15 | 17 | 18 | 19 | 20 | 21 | 22 | 26 | 29 | 34 | 35 |
|---|---|---|---|---|---|---|---|---|---|---|---|
| Guinea Pig (g) No. 1 (%) Clinical findings | 380 123 | 315 102 | 290 94 | 265 86 | 240 77 | 230 74 3 | 225 73 D | | | | |
| Guinea Pig (g) No. 2 (%) | 435 139 | 385 123 | 345 111 | 305 98 | 286 92 | | | | | | |

TABLE 5-continued

Body Weight Gain in EAE Guinea Pigs of Group V Treated with FTS
(50 μg/day, animal)

| Clinical findings | | | 2 | 3 | D | | | | | | |
|---|---|---|---|---|---|---|---|---|---|---|---|
| Guinea Pig (g) | 465 | 445 | 455 | 445 | 467 | 470 | 470 | 507 | 525 | 535 | 540 |
| No. 3 (%) | 153 | 146 | 149 | 149 | 153 | 154 | 154 | 166 | 172 | 175 | 177 |
| Clinical findings | | | | | | | | | | | |
| Guinea Pig (g) | 460 | 445 | 435 | 460 | 470 | 485 | 485 | 525 | 555 | 570 | 565 |
| No. 4 (%) | 151 | 146 | 143 | 151 | 154 | 159 | 159 | 172 | 182 | 187 | 185 |
| Clinical findings | | | | | | | | | | | |

Data for Days 2, 3, 6, 16, 23, 25, 30, 32 omitted.
↑: FTS injection.

TABLE 6

Histopathological Findings in EAE Guinea Pigs Treated with FTS in Varied Doses

| Group | Dose μg/day, animal | No. of animals | Average days for the first EAE sign after immunization | Days after immunization when death occurred in an animal | Histopathological findings in EAE guinea pigs treated with FTS in varied doses | | | |
|---|---|---|---|---|---|---|---|---|
| | | | | | cerebrum | cerebellum | brainstem | spinal cord |
| I | 0 | 1 | 10 | 16 | +~++ | + | +++ | ++ |
| II | 10 | 1 | 21 | >30 | + | 0 | + | 0 |
| | | 2 | no anomaly | >30 | + | + | + | + |
| | | 3 | 17 | >30 | + | 0 | 0 | 0 |
| IV | 50 | 1 | no anomaly | >35 | ++~+++ | ++ | ++~+++ | +++ |
| | | 4 | no anomaly | >35 | + | + | ++ | + |
| V | 50 | 3 | no anomaly | >35 | +~++ | + | + | + |
| | | 4 | no anomaly | >35 | + | + | ++ | + |
| | | 5 | no anomaly | >35 | 0 | 0 | 0 | + |
| VI | 50 | 3 | no anomaly | >35 | ++ | + | ++ | ++ |
| | | 4 | no anomaly | >35 | ++ | ++ | ++ | ++ |
| | | 5 | no anomaly | >35 | ++~+++ | ++ | ++ | ++ |

Experiment 4 Effect of FTS on EAE Monkeys (i) EAE induction

A spinal chord extract obtained from a monkey was mixed with an equal volume of a phosphate buffered physiological saline solution for preparing a spinal chord homogenate (antigen solution). 1.5 ml of the antigen solution was then mixed with the same volume of Freund's complete adjuvant containing 1 mg of killed mycobacterium tuberculosis AOYAMA B and the resultant emulsion was inoculated i.m. to an animal in both temporal muscles (immunization, Day 0).

(ii) Animals

Female crab eating monkeys (*Macaca irus*) weighing 5–6 kg were employed.

(iii) FTS administration

The immunized animals were carefully observed for clinical changes. Whenever an animal showed either a pertinent general appearance or a clinical sign, FTS was administered, dissolved in a solution of mixed essential amino acids or electrolytes, by intraperitoneal or subcutaneous injection. When an animal did receive a dose of FTS, no more additional doses were administered to that animal during the same day.

(iv) Evaluation of results

Neurological signs observed in the animals were graded as follows.

| Neurological signs | | | | |
|---|---|---|---|---|
| 1. General appearance | | | | |
| | 1) | gait | normal | 0 |
| | | | depressed | +1 |
| | | | death | +7 |
| | 2) | appetite | normal | 0 |
| | | | low appetite | +1 |
| | 3) | dystropy | | +1 |
| 2. Clinical signs | | | | |
| | 1) | partial paralysis | | |
| | i) | paralysis in the upper part of body | risable | +2 |
| | | | not risable | +3 |
| | ii) | paralysis in lower part of body | risable | +2 |
| | | | not risable | +3 |
| | iii) | right or left side paralysis | risable | +4 |
| | | | not risable | +5 |
| | 2) | paralysis in four limbs | | +6 |
| | 3) | paropsis | | +1 |

-continued

Neurological signs (visual disorders)

(v) Results of individual monkeys

Monkey 1.

The animal was found on Day 24 to be depressed (+1) with hemiplegia in the right hind leg and astasia (+3). Daily FTS treatment in a 2 mg dose i.p. was commenced on Day 24, and continued until Day 31. The animal regained spirits (no depression) from Day 29 (0) and began to take some food. The ability to rise on four limbs was recovered on Day 31 (+2). A minor paralysis still remained but the animal began to run about; so that, FTS treatment was discontinued from Day 32. The total amount of FTS administered for these eight days was 2 mg×8, or 16 mg.

The animal continued in good spirits until Day 38 though a trace of paralytic trait still remained.

The animal lost appetite, however, on Day 39 (+1) showing some dystropy (+1) and died on Day 40 (+7).

The duration of the interval between the first appearance of EAE (Day 24) and the day of death (Day 40) was 16 days, a relatively longer period compared to other EAE monkeys. This effect was considered to suggest an effect of FTS in prolonging the life of EAE animals.

Monkey 2

On Day 16 the animal fell into low spirits (depression) (+1) presenting mydriasis and paropsis (+1) and this condition continued until the next day. On Day 18 the animal received an injection of 4 mg FTS. However, the animal went into a coma during Day 18 and died on Day 19 (+7).

Monkey 3

The animal was depressed on Day 43, developing hemiplegia in the right side of the body and an inability to rise (+5) so that an injection of 6 mg FTS was given. Normal functioning was recovered on Day 44 (0) with a significant appetite (0). FTS administration was continued at a dose of 4 mg. On Day 45, appetite was again lost (+1) so that the daily FTS treatment was continued at the 1 mg/day level. On Day 46 appetite was revived again (0) but the condition took a sudden turn for the worse and death came on Day 47 (+7).

Monkey 4

The animal became droopy on Day 43 (+1) and still appeared depressed on Day 44 (+1) characterized by simply repeating the same behavior (climbing up a height and never coming down) suggesting some cerebellar disorder (+2). FTS was administered in a dose of 2 mg on Day 44 and in a dose of 1 mg on Days 45 through 47. The animal seemed to recover spirits from Day 45 (0) though a paralysis was maintained in the upper part of the body. On Day 51 the left upper eyelid began to droop (+1) so that FTS treatment was resumed at a 1 mg/day dose from Day 51 and continued through Day 54. Paropsis however did not disappear and death came on Day 54 (+7).

Monkey 4 was another case of an extended survival which lasted from Day 44 (the first manifestation of an EAE sign) to Day 54 (death) and which was considered to reflect the life-prolonging effect of FTS.

Monkey 5

The animal fell into depression on Day 23 (+1), received a 2 mg dose of FTS and seemed on Day 24 to have recovered (0). On Day 30, however, the animal became droopy once again (+1) presenting a certain degree of paropsis (+1) so that FTS was administered at a dose of 2 mg which caused the animal to revive in good spirits on Day 31 (0). On day 38, however, the animal fell again into depression (+1) and was administered 2 mg FTS which caused the animal to revive in spirits. The animal seemed to have recovered completely from EAE. However, on Day 62 it suddenly lost appetite (+1) and developed hemiastasia sinistra (+5). 1 mg FTS was administered but, on Day 63, it developed general paralysis (+6) so that the animal was sacrificed for performing an autopsy. The EAE in this case was considered to be of a recurrent type.

Monkey 6

On Day 67 the animal was found to be out of spirits (+1) so that 2 mg FTS was administered. Appetite was lost on Day 68 (+1). FTS treatment in a dose of 1 mg/day was continued for Days 68 and 69. On Day 69, However, the animal developed general paralysis and died (+7).

Monkeys 2, 3 and 6 were cases where FTS was administered in a lower total amount, was divided in a less frequent administration and where death came faster, specifically, within 1–3 days after the start of FTS administration. The progress in these monkeys from the first manifestation of an EAE sign, and the development symptoms thereafter to death were quite similar to those observed in control monkeys 7–10 as described below.

Monkey 7 (control)

Thirty-six days after immunization, this animal suddenly showed a turn for the worse and died.

Monkey 8 (control)

This animal developed hemiplegia astasia dextra on Day 99 after immunization (+1) and died two days later.

Monkey 9 (control)

This animal developed paralysis in the upper part of the body on Day 73 (+1) and died two days later.

Monkey 10 (control)

This animal developed hemiplegia astasia dextra in a hind leg on Day 41 (+3) and died the next day.

In the EAE system in the monkeys of Experiment 4, the interval between the injection of an emulsion of the spinal chord (immunization) and the first manifestation of a clinical EAE sign varied more as compared to the case of guinea pigs although, once a sign did manifest (paropsis, hemi-or general ataxia or paralysis) the animal died within a period of 1–3 days similar to the case of guinea pigs. In immunized monkeys, if no FTS treatment nor any drug was administered, the first sign of clinical EAE occurred within from 36 to 100 days after the immunization.

In Experiment 4, FTS was investigated in crab eating monkeys for its effects on prolongation of life after the injection of basic protein of spinal chord (immunization) and as a curative of EAE. Unlike the guinea pigs of Experiments 1 and 2 that received the first FTS treatment in advance of the onset of the clinical signs of EAE, monkeys of Experiment 4 were given FTS treatment only after the manifestation of the symptom of EAE. FTS injection in a dose of between 1 and 6 mg/day per monkey significantly prolonged the life of each EAE animal. Had the EAE monkeys been treated with FTS prior to or even immediately after immunization with an emulsion of spinal chord as in the case of guinea pigs, the timing for the first sign of clinical EAE could be considerably delayed.

The efficacy of FTS in prolonging the life of EAE animals and acting as a treatment of EAE which was successfully confirmed in experiments employing monkeys, a species of animals considered to be more close to humans, show the usefulness of FTS in the therapy of multiple sclerosis and other immunodeficiencies.

Experiment 5 Effect on 50 µg FTS Administered to Experimental Allergic Neuritis (EAN) Lewis Rats (i) EAN induction The myelin of the bovine sciatic nerve root was employed as the EAN inducing antigen. It was extracted according to the method of Autilio et al. (L. A. Autilio et al., J. Neurochemistry, 11, 17, 1964) and emulsified in an equal volume of Freund's complete adjuvant and injected into the foot pads of Lewis rats.

(ii) Animals

Male Lewis rats, 6 weeks of age and weighing 170±30 g, were used.

(iii) FTS administration

The-day of inoculation with the myelin was taken as Day 0. Daily treatment of the animals was commenced on Day 6 and was maintained to Day 35 with FTS s.c. injection once a day at a dose of 50 µg per animal, dissolved in a phosphate buffered physiological saline solution.

(iv) Evaluation of the therapeutical effects

The myelin-inoculated animals, when no curative treatment was given, generally showed a weight loss from about 13 to 14 days after the inoculation followed by some ataxia and then paralysis in the hind part of the body. The progress of the symptoms in the animals of FTS-inoculated and non-inoculated (control) groups were registered in numerical expressions according to the following scoring schedule.

| Scoring of Clinical Symptoms | |
|---|---|
| 0 | no clinical disease |
| 1 | a reduced motility accompanying a body weight loss |
| 2 | hind limb weakness |
| 3 | hind limb paralysis |
| 4 | death |

(v) Results

Whereas the average day of first appearance of EAN symptoms was Day 14.3 in the control animals receiving no FTS treatment, three out of eight FTS-treated animals presented no clinical signs at all throughout the 35 days of the experiment manifesting the EAN-suppressing effect of FTS. The average day of first appearance of symptoms in the remaining five animals of the treatment group was Day 17.8 showing a significant retardation of onset as compared to the control animals.

In some animals of the non FTS-treated group, the motility reaction weakness and ataxia gradually disappeared on subsequent days and the animals eventually returned to normal. The average interval between onset and recovery of normal condition was 15.6 days or greater in the non-treated animals while that of the FTS treated animals was an average of 4.6 days. The efficacy of daily FTS administration from Day 6 at a dose of 50 µg/day/animal in quickly suppressing or eliminating the symptoms of the neurological disturbance in the rats and restoring normal conditions is very obvious. These results are summarized in Table 7.

TABLE 7

Effects of 50 µg FTS Administered to EAN Lewis Rats

| Group | Dose µg/animals | No. of animals | The day of the first clinical sign for each animal | Average days for the first clinical sign for animals after inoculation per group | Interval***between day of the first clinical sign and recovery | Average interval for animals per group |
|---|---|---|---|---|---|---|
| I | 0 | 14 | 13, 14, 14 15, 14, 13, 14, 14, 16, 14, 14, 17, 14, 14 | 14.3 ± 1.1* | >22, 17, 11, 19, 12 >22, 13, 18, 12, 16 15, 9, 13, 19 | >15.6 ± 4.1** |
| II | 50 | 8 | No clinical sign, 18, 18 No clinical sign, 18, 18 No clinical sign, 17 | 17.8 ± 0.4* | 1, 4 9, 4 5 | 4.6 ± 2.9** |

*Significance in difference between groups I and II: p<0.001 by student's t-test.
**Significance in difference between groups I and II: p<0.001 by student's t-test.
***Experiment closed on Day 35.

Since EAN is being considered as the animal model for the Guillain-Barré syndrome, immune peripheral neuropathy, polyneuritis etc., and other immune demyelinating diseases, the findings described above are considered to show the therapeutical usefulness of FTS in treating these types of illness in humans.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim:

1. A method for the treatment of Guillain-Barre syndrome comprising administering to a host an effective Guillain-Barre syndrome treating amount of serum thymic factor consisting of a nonapeptide of natural origin having an amino acid sequence of p-Glu-Ala-Lys-Ser-Gln-Gly-Gly-Ser-Asn-OH, wherein p-Glu represents pyroglutamic acid, Ala represents alanine, Lys represents lysine, Ser represents serine, Gln represents glutamine, Gly represents glycine, and Asn represents asparagine.

2. A method for the treatment of inflammatory neuropathy comprising administering to a host an effective inflammatory neuropathy treating amount of serum thymic factor consisting of a nonapeptide of natural origin having an amino acid sequence of p-Glu-Ala-Lys-Ser-Gln-Gly-Gly-Ser-Asn-OH, wherein p-Glu represents pyroglutamic acid, Ala represents alanine, Lys represents lysine, Ser represents serine, Gln represents glutamine, Gly represents glycine, and Asn represents asparagine.

* * * * *

UNITED STATES PATENT AND TRADEMARK OFFICE
CERTIFICATE OF CORRECTION

PATENT NO. : 5,464,816
DATED : Nov. 7, 1995
INVENTOR(S) : Yoshitaka Nagai et al.

It is certified that error appears in the above-indentified patent and that said Letters Patent is hereby corrected as shown below:

Title page, item "[63]" following "Patent No. 5,112,810" insert the following: --, which is a continuation of Ser. No. 420,617, Sept. 21, 1982, abandoned. --

Title page, item "[30]" as follows.

-- [30]   Foreign Application Priority Data

Sep. 22, 1981 [JP]   Japan ........................56-148725   --

Signed and Sealed this

Second Day of July, 1996

Attest:

BRUCE LEHMAN

Attesting Officer    Commissioner of Patents and Trademarks